US006391285B1

(12) United States Patent
Hillman

(10) Patent No.: US 6,391,285 B1
(45) Date of Patent: May 21, 2002

(54) ANTIMICROBIAL POLYPEPTIDE AND METHODS OF USE

(75) Inventor: Jeffrey D. Hillman, Gainsville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 09/361,900

(22) Filed: Jul. 27, 1999

Related U.S. Application Data

(62) Division of application No. 08/871,924, filed on Jun. 10, 1997, now Pat. No. 5,932,469.

(51) Int. Cl.$^7$ .......................... A61K 7/28; A61K 38/16; C07K 14/315
(52) U.S. Cl. .............................. 424/50; 514/13; 530/326
(58) Field of Search .................................. 530/350, 326; 514/12, 13; 424/49, 50

(56) References Cited

U.S. PATENT DOCUMENTS

| | | | |
|---|---|---|---|
| 3,031,446 | A | 4/1962 | Zimmer et al. |
| 3,968,233 | A | 7/1976 | Garzia |
| 4,474,801 | A | 10/1984 | Garzia |
| 5,239,088 | A | 8/1993 | Hoffman et al. |
| 5,352,450 | A | 10/1994 | Koga |
| 5,401,857 | A | 3/1995 | Grey et al. |
| 5,650,320 | A | 7/1997 | Caufield |
| 5,843,709 | A | 12/1998 | Entian et al. |

FOREIGN PATENT DOCUMENTS

| | | |
|---|---|---|
| EP | 0543195 | 5/1993 |
| WO | WO9640865 | 12/1996 |
| WO | WO9817685 | 4/1998 |

OTHER PUBLICATIONS

European Search Report for European Patent application 98928967.3–2106–US9812003, 2001.
Gutierrez et al., Insertional mutagenesis and recovery of interrupted genes of *Streptococcus mutan* by using transposon Tn917: Preliminary characterization of mutants displaying acid sensitivity and nutritional requirements, J. Bact. 178:4166–4175 (1996).
EMBL database entry AAP91366, 1992.
Mota–Meira et al., Purification and structure of mutacin B–Ny266: a new lantibiotic produced by *Streptococcus mutans*. FEBS Lett 1997 Jun. 30; 410(2–3):275–9.
Hillman et al. Genetic and biochemical analysis of mutacin 1140, a lantibiotic from *Streptococcus mutans*. Infection & Immunity, Jun. 1998, p. 2743–2749.
Smith et al. Covalent structure of mutacin 1140 and a novel method for the rapid identification of lantibiotics. Eur. J. Biochem. 267:6810–6816 (2000).
Beppu, T., "Genes, enzymes and secondary metabolites in industrial microorganisms," *Journal of Industrial Microbiology*, 16:360–363 (1996).
Chikandas, Michael L., et al., "Mutacin II, a Bactericidal Lantibiiotic from *Streptococcus mutans*," *Antimicrobial Agents and Chemotherapy*, 39(12):2656–2660 (Dec. 1995).
Hillman, Jeffrey D., et al., "Isolation of a *Streptococcus mutans* Strain Producing a Novel Bacteriocin," *Infection and Immunity*, 44(1):141–144 (Apr. 1984).
Novák, J., et al., "Isolation and Biochemical Characterization of a Novel Lantibiotic Mutacin from *Streptococcus mutans*," *Journal of Bacteriology*, 176(14):4316–4320 (Jul. 1994).
Novák, Jan, et al., "Detection of Modified Amino Acids in Lantibiotic Peptide Mutacin II by Chemical Derivatization and Electrospray Ionization—Mass Spectroscopic Analysis," *Analytical Biochemistry*, 236:358–360 (1996).
Passador, Luciano, et al., "Functional Analysis of the *Pseudomonas aeruginosa* Autoinducer PAI," *Journal of Bacteriology*, 178(20):5995–6000 (Oct. 1996).
Schaefer, Amy L., et al., "Quorum Sensing in *Vibrio fischeri*: Probing Autoinducer–LuxR Interactions with Autoinducer Analogs," *Journal of Bacteriology*, 178(10):2897–2901 (May 1996).

Primary Examiner—Gary L. Kunz
Assistant Examiner—Stephen Gucker
(74) Attorney, Agent, or Firm—McDonnell Boehnen Hulbert & Berghoff

(57) ABSTRACT

Antimicrobial compounds and compositions and uses thereof, including the treatment and prevention of bacterial infections are described. The compounds and compositions include lantibiotic polypeptides and the nucleic acid sequences encoding the polypeptides. The compounds and compositions are useful as antimicrobials in antibiotic pharmaceutical preparation and as an antimicrobial or antiseptic dentifrice.

11 Claims, 1 Drawing Sheet

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 1316 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: -35_signal
      (B) LOCATION: 738..742

(ix) FEATURE:
      (A) NAME/KEY: -10_signal
      (B) LOCATION: 757..763

(ix) FEATURE:
      (A) NAME/KEY: RBS
      (B) LOCATION: 784..791

(ix) FEATURE:
      (A) NAME/KEY: CDS (B) LOCATION: 796..987

(xi) SEQUENCE DESCRIPTION: SEQ ID NO:1:

AATCTATTTT GTAGAGAATT TAGAGAAATT ATTAAATTAC CAAGATATGT TTGCAATAAC      60

ATTTTTAAAA TTTTTAAAAA AAATTATTAC TTACTTTCAT GATAAGTCAG TAGATATGTC     120

TGAATTAGAA CATTATATTA ATATAGTTGA AGAAATAAAT CCTACGATTG CTTCAATTCT     180

TAAATCTAAT TTGAATCAGC TTTTATAAAG TTTTAGCCAT TAAAGCCATC TTGATAAATT     240

TTATATCTTT CATATTCATT AAATGTGGAG ATAATGAAAA AGCAACGGTT ATGCTATCGC     300

TGCTTTTTTT GTGATTAGAA GCTATGTTAT CATGGAGTTA TAGTAATGAA ACATAGTGAC     360

AGTTCATCCT TTCTTATTAT AAAAGTGGTA ATAAGAAAG TGGTAAACAA AGAGTTAGTA      420

AAATAATACG TTTAACCATA ATATTTCCTC CTTTAATTTA TTATAAGATT CAAAAAGGTA    480

ATATTCCTAT ATTTGCAAAT ATGGGATAAA ATAATTTTAA AAAAGCAGAT TTGCAATTTT    540

AAAAAAATAG AGGCTAATGG TGGTATTATA TTATTGTAAA TATATGTTTA CTCAGTAATA    600

GTGATTTACT ATTACAACAG ATTTTGTTGT TATCTTAGAT ATTTCTGCTA GCATTAGTTA    660

TCTGTAGATG TACTACTTAA TAAGTATATA ATTATAATTA TATAATAACT ATTATCAGAT    720

TACCGTTAAA AGTTTTCTGA TATGCTTCTA CTGAACAATT TATGTTCAGT TACACACATG    780

AAAAAGGAGG ATATT ATG TCA AAC ACA CAA TTA TTA GAA GTC CTT GGT ACT      831
              Met Ser Asn Thr Gln Leu Leu Glu Val Leu Gly Thr
                1               5                  10

GAA ACT TTT GAT GTT CAA GAA GAT CTC TTT GCT TTT GAT ACA ACA GAT       879
Glu Thr Phe Asp Val Gln Glu Asp Leu Phe Ala Phe Asp Thr Thr Asp
         15                  20                  25

ACT ACT ATT GTG GCA AGC AAC GAC GAT CCA GAT ACT CGT TTC AAA AGT       927
Thr Thr Ile Val Ala Ser Asn Asp Asp Pro Asp Thr Arg Phe Lys Ser
     30                  35                  40

TGG AGC CTT TGT ACG CCT GGT TGT GCA AGG ACA GGT AGT TTC AAT AGT       975
Trp Ser Leu Cys Thr Pro Gly Cys Ala Arg Thr Gly Ser Phe Asn Ser
 45                  50                  55                  60

TAC TGT TGC TGA TTGTATAAAA GATTTAGATT GTGCCGCATG TTAGCGGCAC          1027
Tyr Cys Cys *

AATCTTTTGA TATTAGAGGT ATTAATATGT TAAATACACA ATTATTAGAA GTCCTTGGTA    1087

CTAAAACTTT TGATGTTCAA GAAGATTTAT TTGAGTTTAA TATAACAGAT ACTATTGTAC    1147

TGCAGGCTAG TGATAGTCCA GATACTCATA GTAGGGGTCC CGAGCGCTTA GTGGGAATTT    1207

GTATCGATAA GGGGTACAAA TTCCCACTAA ACCAATGTTT CAAGGCCTAT TTATTTTTTA    1267

TATTCAATTC TCTTAAGTGT TTAGGAATAG ATAACAAGTC AAATTTATA               1316

(2) INFORMATION FOR SEQ ID NO:2:

(i) SEQUENCE CHARACTERISTICS:
        (A) LENGTH:  63 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Asn Thr Gln Leu Leu Glu Val Leu Gly Thr Glu Thr Phe Asp
 1               5                  10                  15

Val Gln Glu Asp Leu Phe Ala Phe Asp Thr Thr Asp Thr Thr Ile Val
             20                  25                  30

Ala Ser Asn Asp Asp Pro Asp Thr Arg Phe Lys Ser Trp Ser Leu Cys
         35                  40                  45

```
Thr Pro Gly Cys Ala Arg Thr Gly Ser Phe Asn Ser Tyr Cys Cys
    50                  55                  60
```

(2) INFORMATION FOR SEQ ID NO:3:

(i) SEQUENCE CHARACTERISTICS:
        (A) LENGTH: 1322 amino acids
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: -35_signal
        (B) LOCATION: 177..182

(ix) FEATURE:
        (A) NAME/KEY: -10_signal
        (B) LOCATION: 191..196

(ix) FEATURE:
        (A) NAME/KEY: RBS
        (B) LOCATION: 218..224

(ix) FEATURE:
        (A) NAME/KEY: CDS
        (B) LOCATION: 228..782

(xi) SEQUENCE DESCRIPTION: SEQ ID NO:3:

```
TAGTAAAGTG GGTAGTTTCA ATATCTGCCC TCCTCGAAAG ATCTCCGTCA GTTTCAATAG        60

TTACTGTTGT TAACTATAAA TTATACTTAA ATTGATAGGA AACTTGGTCG TGACATTATC       120

ATATGTTGAT ATTGGAAGAG AATCAAATTT ATAAAGACAA TTAAATCTAA ATTTGATGAA       180

TATTTAGATG AATTATTACT AGGTTGACAG TCATGTTAGG AGAAGAG ATG AAC GAT         236
                                                 Met Asn Asp
                                                         65

TTT CAA TTT CAA GAT TAT TTT ATG TAC AGA AAA CCA TTA GGC AAC TTT         284
Phe Gln Phe Gln Asp Tyr Phe Met Tyr Arg Lys Pro Leu Gly Asn Phe
        70                  75                  80

TCT AAT TTT TTT AGT ATA ACT GAT ACG ATG GAT CCC ATT GAG TTA CTA         332
Ser Asn Phe Phe Ser Ile Thr Asp Thr Met Asp Pro Ile Glu Leu Leu
    85                  90                  95

CAT AGT GAT CCG ATA TTT GCT GAA GGA GTA TAT TTG GCC TCT TCA TCT         380
His Ser Asp Pro Ile Phe Ala Glu Gly Val Tyr Leu Ala Ser Ser Ser
100                 105                 110                 115

CTT AGA GCA GCC ATA AAT AAA CTT AAG AAT CAT ACT GCG AGT ACT AAG         428
Leu Arg Ala Ala Ile Asn Lys Leu Lys Asn His Thr Ala Ser Thr Lys
                120                 125                 130

GAT AAA AAG AAT GCA AGA GAG ACT ATT TTT CAA TAC TAT GCC CGT TAT         476
Asp Lys Lys Asn Ala Arg Glu Thr Ile Phe Gln Tyr Tyr Ala Arg Tyr
            135                 140                 145

AAC ACG AGA TCA ACT CCG TTT GGC TTG TTT TCG TCC ATC GGA GTA GGT         524
Asn Thr Arg Ser Thr Pro Phe Gly Leu Phe Ser Ser Ile Gly Val Gly
        150                 155                 160

GCT TTT TCG GCT TAC CTT AAA AAA GAA AAG TCT CGT TAT GAA AAA TCT         572
Ala Phe Ser Ala Tyr Leu Lys Lys Glu Lys Ser Arg Tyr Glu Lys Ser
    165                 170                 175

ATT AAT ATT GAT CTT TTT TGG GCT TAT AAA GTA GCA GAT AAA CTA GAA         620
Ile Asn Ile Asp Leu Phe Trp Ala Tyr Lys Val Ala Asp Lys Leu Glu
180                 185                 190                 195

AGT ATG CCT GAA ATT TTA AAT ACT TTA AAA GTA GTT GCT AAT AAT GCT         668
Ser Met Pro Glu Ile Leu Asn Thr Leu Lys Val Val Ala Asn Asn Ala
                200                 205                 210
```

```
TTG CAA AAG TCA GAT AAT TTT TGG CTT TTG GAT ACG CGA AGT CAT TTT      716
Leu Gln Lys Ser Asp Asn Phe Trp Leu Leu Asp Thr Arg Ser His Phe
            215                 220                 225

GGT CTT ATG AAT TCT TTT CAT TTT ATC TTG TAC GAC TTC TAT TCT TTC      764
Gly Leu Met Asn Ser Phe His Phe Ile Leu Tyr Asp Phe Tyr Ser Phe
        230                 235                 240

CTT CAA GAT AGA CCA TAA GAATTGATAT ATCAGCTGGA TTCACACCAG              812
Leu Gln Asp Arg Pro
    245

AAATACGGCT AGCTTGACCA ATAGTTTCTG GGTTAATTTT CTTAAATTTC TGACGTGCTT     872

CGGTCGCAAT AGAATCAATG GCATCCCAAT CGATATTCTT AGGAATTCGA GCTCGGTACC     932

CGGGGATCCT CTAGAGTCGA CCTGCAGGCA TGCAAGCTTG GCACTGGCCG TCGTTTTACA     992

ACGTCGTGAC TGGGAAAACC CTGGCGTTAC CCAACTTAAT CGCCTTGCAG CACATCCCCC    1052

TTTCGCCAGC TGGCGTAATA GCGAAGAGGC CCGCACCGAT CGCCCTTCCC AACAGTTGCG    1112

CAGCCTGAAT GGCGAATGGC GCCTGATGCG GTATTTTCTC CTTACGCATC TGTGCGGTAT    1172

TTCACACCGC ATATGGTGCA CTCTCAGTAC AATCTGCTCT GATGCCGCAT AGTTAAGCCA    1232

GCCCCGACAC CCGCCAACAC CCGCTGACGC GCCCTGACGG GCTTGTCTGC TCCCGGCATC    1292

CGCTTACAGA CAAGCTGTGA CCGTCTCCGG G                                   1323

(2) INFORMATION FOR SEQ ID NO:4:

(i) SEQUENCE CHARACTERISTICS:
        (A) LENGTH: 184 amino acids
        (B) TYPE: amino acid
        (D) TOPOLOGY: linear (ii) MOLECULE TYPE: protein (xi) SEQUENCE DESCRIPTION: SEQ ID NO:4:

Met Asn Asp Phe Gln Phe Gln Asp Tyr Phe Met Tyr Arg Lys Pro Leu
 1               5                  10                  15

Gly Asn Phe Ser Asn Phe Phe Ser Ile Thr Asp Thr Met Asp Pro Ile
            20                  25                  30

Glu Leu Leu His Ser Asp Pro Ile Phe Ala Glu Gly Val Tyr Leu Ala
        35                  40                  45

Ser Ser Ser Leu Arg Ala Ala Ile Asn Lys Leu Lys Asn His Thr Ala
    50                  55                  60

Ser Thr Lys Asp Lys Lys Asn Ala Arg Glu Thr Ile Phe Gln Tyr Tyr
65                  70                  75                  80

Ala Arg Tyr Asn Thr Arg Ser Thr Pro Phe Gly Leu Phe Ser Ser Ile
                85                  90                  95

Gly Val Gly Ala Phe Ser Ala Tyr Leu Lys Lys Glu Lys Ser Arg Tyr
            100                 105                 110

Glu Lys Ser Ile Asn Ile Asp Leu Phe Trp Ala Tyr Lys Val Ala Asp
        115                 120                 125

Lys Leu Glu Ser Met Pro Glu Ile Leu Asn Thr Leu Lys Val Val Ala
    130                 135                 140

Asn Asn Ala Leu Gln Lys Ser Asp Asn Phe Trp Leu Leu Asp Thr Arg
145                 150                 155                 160

Ser His Phe Gly Leu Met Asn Ser Phe His Phe Ile Leu Tyr Asp Phe
                165                 170                 175

Tyr Ser Phe Leu Gln Asp Arg Pro
            180                 185
```

-continued

```
(2) INFORMATION FOR SEQ ID NO:5:

(i) SEQUENCE CHARACTERISTICS:
        (A) LENGTH: 21 amino acids
        (B) TYPE: amino acid
        (D) TOPOLOGY: linear (ii) MOLECULE TYPE: protein (ix) FEATURE:
        (A) NAME/KEY: MOD_RES
        (B) LOCATION:  3
        (D) OTHER INFORMATION:   Xaa =', -didehydroalanine (ix) FEATURE:
        (A) NAME/KEY: MOD_RES
        (B) LOCATION:  8
        (D) OTHER INFORMATION:   Xaa =', -didehydrobutyrine (ix) FEATURE:
        (A) NAME/KEY: MOD_RES
        (B) LOCATION:  14
        (D) OTHER INFORMATION:   Xaa = Abu (xi) SEQUENCE DESCRIPTION: SEQ ID NO:5:

Phe Lys Xaa Trp Ala Leu Ala Xaa Pro Gly Ala Ala Arg Xaa Gly Ala
 1               5                  10                  15

Phe Asn Ala Tyr Ala
             20
```

ANTIMICROBIAL POLYPEPTIDE AND METHODS OF USE

CROSS-REFERENCE TO RELATED APPLICATIONS

This is a division of application Ser. No. 08/871,924, filed Jun. 10, 1997, now U.S. Pat. No. 5,932,469.

BACKGROUND OF THE INVENTION

The subject invention was made with government support under a research project supported by National Institute of Dental Research Grant No. DE04529. The government has certain rights in this invention.

The subject invention concerns novel polypeptides and nucleic acid sequences encoding those polypeptides. The polypeptides are related to bacteriocins, e.g. mutacins, produced by microbes for providing a selective advantage for the microbe. The invention includes methods of use which exploit the advantageous activities or properties of the polypeptides or nucleic acid sequences.

The phenotypically similar bacteria collectively known as the mutans streptococci are considered major etiologic agents responsible for dental caries. The species most commonly associated with human disease is *Streptococcus mutans*. Pathogenicity of *S. mutans* includes the ability to produce antimicrobial substances generally referred to as bacteriocin-like inhibitory substances (BLIS) or bacteriocins. Bacteriocins produced by *Streptococcus mutans* are known as mutacins. These substances are produced by microorganisms to provide a selective force necessary for sustained colonization in a milieu of densely packed competing organisms found in dental plaque.

To date, most bacteriocins remain only partially characterized because they are made in small quantities and only under special cultivation conditions. In addition, mutacins are known to be difficult to isolate from liquid medium. The spectrum of activity and chemical and physical properties of mutacins can vary widely.

Certain bacteriocin peptides or mutacins produced by *S. mutans* group II have recently been characterized as belonging to a group of peptides called lantibiotics. Novak, et al. (1996) *Anal. Biochem.* 236:358–360. Lantibiotics are polycyclic peptides which typically have several thioether bridges, and which can include the amino acids lanthionine or β-methyllanthionine. In addition, lantibiotics can contain a, β-unsaturated amino acids such as 2,3-didehydroalanine and 2,3-didehydro-2-aminobutyric acid, which are the products of post-translational modification of serine and threonine residues, respectively.

Certain lantibiotics have demonstrated antibiotic activity, mainly against Gram-positive bacteria (Bierbaum and Sahl (1993) *Int. J. Med. Microbiol. Virol. Parasitol. Infect. Dis.* 278:1–22). Nisin and epidermin are the best known examples of the 20 or so lantibiotics which have been identified to date. They are ribosomally synthesized as prepropeptides that undergo several post-translational modification events, including dehydration of specific hydroxyl amino acids and formation of thioether amino acids via addition of neighboring cysteines to didehydro amino acids. Further post-translational processing involves cleavage of a leader sequence, which can be coincident with transport of the mature molecule to the extracellular space. A mature lantibiotic molecule is usually about 20 to 35 residues in which the thioether linkages result in cyclical segments that provide a substantial degree of rigidity to the rodlike structure.

Current evidence indicates that the biological activity of certain lantibiotics, e.g., those known as "type" lantibiotics, depends on the association of a number of molecules with the membrane of a target bacterium to form ion channels, thereby resulting in desynergization. Rapid loss of all biosynthetic processes occurs, resulting in death of the target cell. Other lantibiotics known as "type B" lantibiotics, can exert their effect by specifically inhibiting certain enzymes.

The genetics of lantibiotic production have been studied in several species of bacteria. In general, it has been found that the structural gene for the preprolantibiotic is clustered with genes which encode products responsible for post-translational modifications of the lantibiotic. In certain instances, these genes are known to form an operon or operon-like structure (e.g., Schnell, et al. (1992) *Eur. J. Biochem.* 204:57–68). Production of lantibiotics also can require accessory proteins, including processing proteases, translocators of the ATP-binding cassette transporter family, regulatory proteins, and dedicated producer self-protection mechanisms. At least seven genes have been shown to be involved in epidermin biosynthesis.

Lantibiotic properties have been exploited in certain products that are commercially available. The lantibiotic, nisin, has been developed as a food preservative which has been given "Generally Recognized as Safe (GRAS)" status by the federal Food and Drug Administration (FDA). It is employed in this fashion in more than 40 countries in preference to nitrites and nitrates. The oral toxicity of this compound, and presumably other lantibiotics, is very low in rats ($LD_{50}$=7 g/kg; Hurst, (1981) *Adv. Appl. Microbiol.* 27:85–123). Other applications for nisin, including its use as a mouth rinse (Howell, et al. (1993) *J. Clin. Periodontal* 20:335–339), are actively being examined by a large number of laboratories.

The discovery of new lantibiotic compounds having antibiotic activity can be particularly important in view of the increased resistance to presently available antibiotics that have been shown in recent years to have developed in certain pathogenic microorganisms. Novel lantibiotic compounds having unique or superior activity against particularly virulent pathogenic bacteria are advantageous in providing new weapons in the arsenal against bacterial infection.

BRIEF SUMMARY OF THE INVENTION

The present invention is summarized in that a novel lantibiotic, here identified as mutacin 1140, has been identified from *Streptococcus mutans*. The lantibiotic mutacin 1140 has a wide spectrum of activity against bacteria of several genera.

The present invention is also summarized by the identification and sequencing of genetic elements associated with the synthesis of the lantibiotic mutacin 1140 in its native host. These genetic elements facilitate the synthesis of the lantibiotic mutacin 1140 in other microbial hosts.

It is yet another object of this invention to provide a method of treatment for human beings or other animals having bacterial infection or infestation. A particular object of the invention is to provide treatment of an animal against infection or colonization by a pathogenic organism that can cause dental caries or other oral pathogenic events. The method of treatment comprises contacting a target microbe with an effective amount of the compound, or a composition comprising that compound, to kill, inhibit, or otherwise control the growth or proliferation of the target microorganism.

Still further, the nucleic acid sequences of the subject invention can be employed in standard genetic engineering procedures to transform appropriate host cells for producing polypeptides according to the subject invention. Other uses for the subject polypeptide or polynucleotide sequences will be recognized by ordinarily skilled artisans in view of currently available knowledge and the description provided herein.

DETAILED DESCRIPTION OF THE INVENTION

Figure 1:
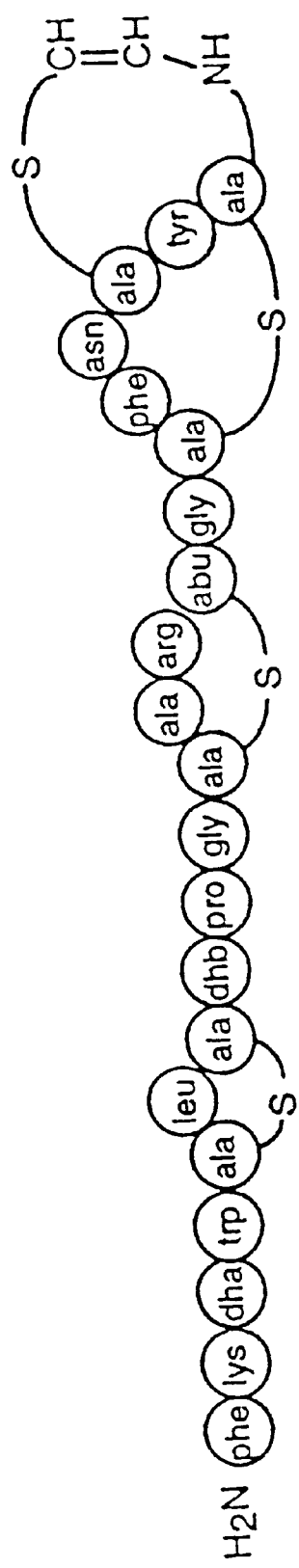
FIG. 1 SEQ ID NO:5, shows a proposed secondary structure of a polypeptide according to the subject invention. Abbreviations of amino acids include the following: ala-S-ala=lanthionine; abu-S-ala=3-methyl anthionine; dha=α,β-didehydroalanine; dhb=α,β-didehydrobutyrine. The C-terminal cysteine is added to dha in position 19 and oxidized to yield a S-aminovinyl-D-cysteine.

Described herein is a novel antibiotic first identified from a strain of Streptococcus mutans designated JH1140. The antibiotic, here termed mutacin 1140, like other lantibiotics, is a polycyclic peptide which is the product of post translational modification of a precursor protein translated from a single gene transcript in the host organism. The identified molecular structure of mutacin 1140 is illustrated in FIG. 1 SEQ ID NO:5.

Lactate-dehydrogenase deficient mutants of Streptococcus mutans have been studied for their potential use in replacement therapy for dental caries. Without the trait of LDH, fermentation of carbohydrates by this microorganism employs alternate pathways for pyruvate metabolism that yields significant amounts of neutral end products, and thus LDH deficient strains exude less total acids into the environment. As a result, LDH deficient mutants of this bacteria are less cariogenic. Thus, these bacterias are being studied as an effector strain for replacement therapy for dental caries. However, in order to be an effective replacement strain, strains must demonstrate superior competitive colonization properties in order to compete against other strains of the species and to prevent subsequent recolonization by wild-type strains. Accordingly, effort hag been conducted to find strains which have both superior colonization properties as well as an LDH-deficiency phenotype.

One of the evolutionary strategies utilized by microorganisms for enhanced competitiveness with competing strains is the synthesis of antibiotic agents to which competitive strains are sensitive. It was found here that a strain of S. mutans, previously called JH1000, an ethyl methane sulfonate-induced mutant called JH1005, and a spontaneous mutant of that strain, known as JH1140, which have been previously reported to have good colonization properties, produced a potent broad spectrum bacteriocin-like inhibitory substance, referred to as a BLIS. As described below, the BLIS was found to inhibit the growth of representative strains of a wide variety of bacterial species. In addition, virtually all known Streptococcus mutans strains tested were sensitive to the BLIS substance.

Analysis of isogenic mutants of these strains demonstrated good correlation between BLIS production and colonization potential in both a rodent model and human subjects. Utilizing genetic methods, the transcript responsible for the BLIS activity has been identified and sequenced. Presented as Sequence ID NO: 1 below is the genomic copy of the single transcript encoding the peptide responsible for the BLIS activity, the gene being named here lanA. Identified as Sequence ID NO: 2 below is the deduced amino acid sequence of the transcript produced by an open reading frame present in Sequence ID NO: 1. Sequence ID NO: 2 is the pre-protein form which, after proteolytic cleavage and other processing by other factors present in the host organism, results in the synthesis of mutacin 1140 as shown in FIG. 1 SEQ ID NO:5.

The proper synthesis of mutacin 1140 in the host microorganism requires the presence of other enzymes to properly process the precursor form of the protein into the effective and active form of the peptide antibiotic. The gene encoding one of those enzymes, here designated lanB, has also been cloned and sequenced and is presented as Sequence ID NO: 3 below. Sequence ID NO: 4 below presents the deduced amino acid sequence of the open reading frame contained in Sequence ID NO: 3.

As used herein, the term "mutacin 1140" is intended to apply to the peptide antibiotic produced by Streptococcus mutans strain 1140, as well as related peptides produced by minor insertions, deletions or other variants which do not detract from the biological efficacy of the lantibiotic. It should be understood that while the chemical structure presented in FIG. 1 SEQ ID NO:5, is believed correct, that due to limitation in the analytical techniques used to date to elucidate the structure of the molecule, it is possible that there may be some minor differences between the structure of FIG. 1 SEQ ID NO:5 and the actual structure of the molecule produced by the bacteria, particularly at the carboxyl-end of the peptide. It is intended that the term mutacin 1140 describes the actual molecule in the event there are such minor differences. It is also anticipated that other evolutionarily-related strains of Streptococcus mutans, or closely related strains of other species, could produce allelic variations of this same lantibiotic and the term mutacin 1140 is intended to cover those as well.

It has been found that mutacin 1140 is an antibiotic with an evolutionary relationship to another antibiotic known as epidermin produced by Staphylococcus epidermidis. The genetic sequence presented below, derived from a mutant strain JH1005 derived from JH1000, includes sequences with a high degree of homology to epiA, B and D, which are genes previously sequenced from Staphylococcus epidermidis and found to be involved in the biosynthesis of the antibiotic epidermin. The lanA and lanB genes presented herein are believed to be roughly analogous to the epiA and epiB genes associated with the antibiotic epidermin.

The antibiotic polypeptide mutacin 1140 of the present invention can be isolated from the culture medium in which its native host organism, i.e., a Streptococcal organism, hag been grown in culture, followed by isolation of the polypeptide antibiotic from the culture medium. In addition, the presentation of the lanA and lanB coding sequences below allows for the construction of artificial genes encoding these sequences which can be transformed into other Streptococcal species or strains of other bacterial species. Two Streptococcal strains which produce the mutacin 1140 antibiotic have been deposited with the American Type Culture Collection, Rockville, Maryland, as Accession Numbers 55676 (JH1140) and 55677 (JH1000). The mutacin 1140 antibiotic can be recovered from these strains, or other related strains of Streptococcal species into which the genetic capability to synthesize mutacin 1140 is introduced using the information from Sequence ID NOS: 1 through 4 below.

A potential complexity in the introduction of the phenotype of production of mutacin 1140 into a new strain is the fact that the peptide undergoes post-translational modifications by other genetic elements in the host strain. As mentioned above, the lanB gene presented below is a necessary, but not sufficient, genetic component for the post translational modification. The other post translational modification genes are contained within the genome of strain JH1140 as deposited above. By performing a random-type genetic transfer experiment of DNA from mutacin 1140-competant hosts into other Streptococcal strains, one can readily identify what other genetic components are necessary, in addition to lanA and lanB presented below, to achieve the fully mature and biologically active form of mutacin 1140 produced by the native producing Streptococcal host strains. Such procedures are within the ordinary level of skill in the art. Once identified, these other genetic components can be transferred together with lanA and lanB into a new host which would then produce mutacin 1140.

It is also specifically envisioned that mutacin 1140 can be synthesized ex vivo. A number of techniques exist for the synthesis of peptide molecules by a relatively conventional organic chemical techniques. For example, solid phase polypeptide synthesis permits the creation of peptides, and that technology has evolved to the point where peptides of the size of mutacin 1140 can readily be synthesized outside of a microbial host.

It is envisioned that the mutacin 1140 antibiotic will be useful generally as an antibiotic. Since the antibiotic is produced by a common streptococcal strain present in human mouths, it is expected to be relatively non-toxic to human species. This conclusion is further buttressed by its analogous characteristic to existing antibiotics, such as epidermin, which are known to be quite non-toxic to mammals. In its method of use, the mutacin 1140 is applied to the area in which it is desired to inhibit microbial growth. A carrier may be used to assist delivery of the antibiotic. In such delivery, it is desired to deliver an effective amount of the lantibiotic, such an effective amount being readily determinable by empirical testing to determine what amount of lantibiotic achieves the desired level of microbial inhibition.

EXAMPLE 1

Purification of a Lantibiotic

A lantibiotic was purified from *Streptococcus mutans* JH1140 using the following procedure:

Four liter batches of Todd-Hewitt broth (THB; Difco) containing 0.5% LE agarose (SeaKem) were sterilized and poured into 90 mm petri plates. The plates were dried overnight at 37° C. A pure culture of JH1140 on a brain-heart infusion starter plate was used to inoculate 3 ml of THB and the cell suspension was vortexed for 10 sec. About 0.3 ml of the cell suspension was spread on the surface of a BHI agar plate and incubated overnight at 37° C. in a candle jar.

A 10-pronged inoculator was ethanol-flame sterilized and used to inoculate JH1140 from the spread plate prepared as above into evenly spaced stabs in the plates prepared as above. The plates were incubated in candle jars at 37° C. for 72 hours. The agar was scraped from the plates entirely and placed into centrifuge bottles. The bottles were stored overnight at −20° C.

The bottles were then centrifuged at room temperature for 60 min. at 4,000 rpm in a Sorvall RC2B centrifuge and then for an additional 30 min. at 8,000 rpm. The supernatant was recovered and passed through Whatman #1 filter paper in a Buchner funnel.

To the filtered extract (ca. 3,000 ml) in a 4 L beaker, 100 ml of chloroform was added. The solution was placed on a magnetic stirrer and agitated at high speed for 120 min. The stir bar was removed and the solution was allowed to stand overnight undisturbed.

The aqueous (upper) phase was aspirated off and discarded. The chloroform layer, containing a milky white flocculent, was divided into 50 ml conical centrifuge tubes and centrifuged at ca. 4,000 rpm for 8 min. Residual aqueous material was removed by aspiration. The clear chloroform layer was removed using a Pasteur pipette, leaving the flocculent which was washed 2 times with 5 ml of chloroform. Chloroform was evaporated from the flocculent using a stream of nitrogen gas; the tube was placed in a 45–50° C. water bath during this process to promote evaporation.

The dried residue was dissolved in 0.5 ml of 50% ethanol; undissolved material was removed by centrifugation at 13,000×g for 2 min. at room temperature. The clarified fraction including the lantibiotic was then stored at −20° C. until further use.

EXAMPLE 2

Bioassay of Lantibiotic Activity

Antimicrobial activity of the lantibiotic was determined by the following procedure:

5 ml of THB were inoculated with S. rattus strain BHT-2 (resistant to 1 mg/ml streptomycin); and grown overnight standing at 37° C. 0.02 ml of fractions to be tested for lantibiotic activity were serially 2-fold diluted in distilled water in microliter wells. Top agar was prepared containing BHI broth, 0.75% agar, 1 mg/ml streptomycin, and 1:10,000 diluted overnight *S. rattus* BHT-2 culture from above at 42° C.; 0.2 ml was pipetted into each microliter well. After 5 min. at room temperature to allow agar to set, the plate was incubated at 37° C. overnight.

The minimal inhibitory concentration (MIC) was determined as the reciprocal of the highest dilution of the test fraction which inhibited growth of *S. rattus* BHT-2 by visual inspection.

EXAMPLE 3

Spectrum of Activity of the Lantibiotic

Single colonies of the strain producing mutacin 1140 were stab inoculated into brain heart infusion medium and incubated overnight in candle jars at 37° C. Three drops of an overnight Todd-Hewitt broth culture of the indicator strain were mixed with 3 ml of molten top agar and poured evenly over the surface of the plate. After an additional 24 hours of incubation, clear zones surrounding the test strain were measured.

Representative strains of various bacteria were tested for their sensitivity to the inhibitory activity of the mutacin 1140 produced by the JH1140 strain by using the overlay technique. In addition to *S. mutans*, most Gram positive organisms were found to be sensitive, including *Streptococcus mitis, Streptococcus pyogenes, Staphylococcus aureus*, and Actinomyces species. The inhibitory factor inhibited 124 of 125 *S. mutans* strains tested. Gram-negative bacteria were invariably resistant to inhibition by mutacin 1140. The following table summarizes the spectrum of activity found for the lantibiotic, The partially purified mutacin 1140 had the same spectrum of activity displayed by JH1140, as demonstrated by spotting 5 $\mu$l samples on lawns of target strains prepared as described above. This is also shown in the table.

TABLE 1

Mutacin Sensitivity Assay[a]

| Indicator Strain | Target Strain | Test Strains JH1140 | Strain JH1005 |
|---|---|---|---|
| Mutans Streptococci | FA1 (a) | + | +/− |
|  | BHT-2 (b) | + | + |
|  | LM7 (e) | + | + |
|  | Ingbritt (c) | + | + |
|  | MT-3 (c) | + | + |
|  | 10449 (c) | + | + |
|  | JC2 (c) | + | + |
|  | GS5 (c) | + | + |
|  | PK1 (c) | + | + |
| Streptococcus salivarius | SS2 | + | + |
|  | O2 | + | + |
|  | O4 | + | + |
| Streptococcus sanguis | Fc-1 | + | + |
|  | KJ3 | + | + |
|  | Challis | − | + |
| Streptococcus mitis | MT | + | + |
|  | RE-7 | + | + |
|  | 26 | + | + |
| Streptococcus pyogenes | STA628 | + | + |
| Streptococcus faecalis | RF | − |  |
| Streptococcus aureus | DC3 | + | + |
| Lactobacillus casei | Lac-6 | − | + |
| Lactobacillus salivarius | UCL-37 | + |  |
| Antinomyces israelii | X523 | + |  |
|  | 10048 | + |  |
| Antinomyces naeslundii | 12104 | + | + |
|  | N16 | + | + |
|  | 6-60B | + | + |
| Antinomyces viscosus | W1528 | + |  |
|  | T6 | + |  |
|  | M100 | + |  |
| Micrococcus luteus | 207-79 | − |  |
| Bacteroides gingivalis | 381 | − |  |
| Wolinella recta | 371 | − |  |
| Capnocytophaga sputigena | 4 | — |  |

[a]Sensitivity to mutacin was determined as described. Indicator strains were evaluated as sensitive (+) showing zones of 10–15 mm in diameter, insensitive (−), or slightly sensitive (+/−) with zones < 5 mm in diameter to test strain.

The inhibitory factor was produced in detectable amounts only during early stationary phase and could be recovered from Todd-Hewitt broth cultures of JH1140. The inhibitory factors effect on other strains of *S. mutans* was bacteriocidal, since loopfuls of agar taken from clear zones were found to be sterile. The inhibitory activity in dell-free culture liquors was completely inactivated by treatment with trypsin under the conditions tested. Incorporation of trypsin inhibitor into the reaction mixture at a concentration of 100 µg/ml prevented this inactivation. The inhibitory activity was inactivated ca. 50% by treatment with 100 mg/ml pronase. Higher concentrations of pronase (250 µg/ml) or more prolonged treatment (1 h) resulted in complete inactivation of the bacteriocin activity. It appeared to be completely resistant to inactivation by DNase I, RNase A, lipases, thermolysin, and lysozyme. The proteinaceous nature of the inhibitor indicated by this experiment, plus its biological activity, formally qualify it for inclusion in the broad family of bacteriocins. The amino acid sequence of the subject bacteriocin polypeptide was determined.

EXAMPLE 4

Characterization of Lantibiotic Peptides

Information on the total number of modified amino acids in a lantibiotic can be determined by a combination of a chemical derivatization and electrospray ionization mass spectroscopy. Edman degradation of ethane thiol-derivatized mutacin 1140 gave the results shown in the following table. This procedure was performed as described by Mezer et al., (1994) *Analyt. Biochem.* 223:185–190.

TABLE 2

Edman Sequencing of Mutacin 1140 Derivatized with Ethanethiol

| Cycle | Predicted Residue | Identified Residue |
|---|---|---|
| 1 | phe | phe |
| 2 | lys | lys |
| 3 | ser | S-EC[a] |
| 4 | trp | trp |
| 5 | ser | S-EC |
| 6 | leu | leu |
| 7 | cys | S-EC |
| 8 | thr | β-M-S-EC[a] |
| 9 | pro | pro |
| 10 | gly | gly |
| 11 | cys | S-EC |
| 12 | ala | ala |
| 13 | arg | arg |
| 14 | thr | β-M-S-EC |
| 15 | gly | gly |
| 16 | ser | S-EC |
| 17 | phe | phe |
| 18 | asn | asn |
| 19 | ser | S-EC |
| 20 | tyr | tyr |
| 21 | cys | ND[b] |
| 22 | cys | ND |

[a]Thioethyl cysteine (S-EC) and β-methylthioethyl cysteine (β-M-S-EC) derived from ethanethiol derivatization of lanthionine (Lan), 3-methyllanthionine (MeLan), 2,3-didehydroalanine (Dha) and 2,3-didehydro-2-aminobutyric acid (Dhb) according to the scheme of Myers as presented below:

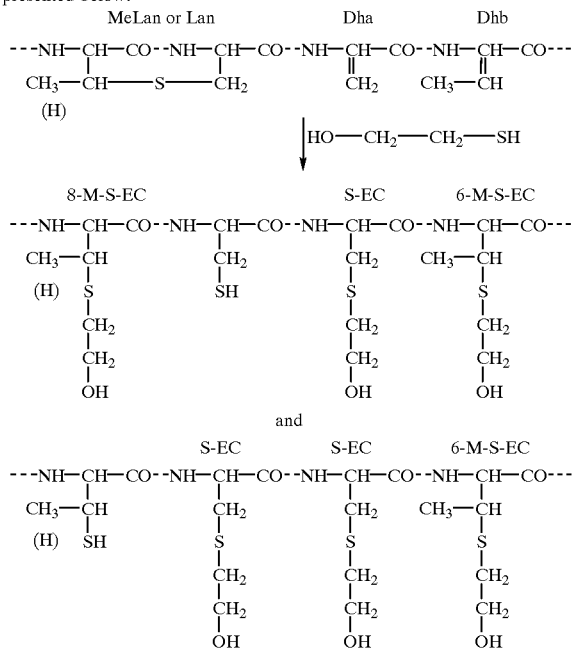

[b]Not detected

These analyses suggested the chemical structure shown in FIG. 1 SEQ ID NO:5.

EXAMPLE 5

Genetic Analysis

A genetic analysis of a strain producing the lantibiotic was performed, The analysis utilized a plasmid pTV1-OK which is a repA (ts) derivative of the *Lactococcus lactis* cryptic plasmid pWV01 for temperature-dependent replication in both *Streptococcus mutans* and *Escherichia coli*. The plasmid possesses the transposon Tn917 which confers erythromycin resistance in streptococci. Transposon mutagenesis was performed on lantibiotic-producing strain JH1005 harboring pTV1-OK. Erythromycin resistant clones were selected on BHI agar using 15 μg/ml antibiotic and were then stab inoculated into the same medium without antibiotic. After incubation overnight in candle jars at 37° C., the plates were overlaid with 3 ml of top agar containing about $10^6$ colony forming units per ml of BHT-2. Stabbed clones which failed to produce growth inhibition of the BHT-2 lawn were recovered and purified by streaking on a medium with erythromycin.

From these mutants, which now had the transposon in the genetic elements responsible for lantibiotic production, chromosomal DNA was isolated and DNA flanking the Tn917 insert was cloned into *Escherichia coli* strain MC1061. The flanking DNA was sequenced by the University of Florida ICBR using Taq Dye Deoxy Terminator and Dye Primer Cycle Sequencing protocols as published by Applied Biosystems, using an Applied Biosystems Model 373A DNA Sequencer. Homology searches were conducted on the recovered sequences using the BLAST program. The recovered sequences, designated lanA and lanB are presented as SEQ:ID NO:1 and SEQ:ID NO:3 below. These sequences were found to have homology to epiA and epiB. The open reading frames of these DNA sequences produce the proteins presented in SEQ:ID NO:2 and SEQ:ID NO:4 below.

EXAMPLE 6

Formulation and Administration

The compounds, polypeptides, and polynucleotides of the invention are useful for various non-therapeutic and therapeutic purposes. It is apparent from the testing that the compounds, polypeptides, and polynucleotides of the invention are effective for biochemical probes or controlling bacterial growth.

Therapeutic application of the new compounds and compositions comprising them can be contemplated to be accomplished by any suitable therapeutic method and technique presently or prospectively known to those skilled in the art. Further, the compounds of the invention have use as starting materials or intermediates for the preparation of other useful compounds and compositions The dosage administration to a host in the above indications will be dependent upon the identity of the infection, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

It should be understood that the examples and embodiments described herein are for illustrative purposes only and that various modifications or changes in light thereof will be suggested to persons skilled in the art and are to be included within the spirit and purview of this application and the scope of the appended claims.

I claim:

1. A composition of matter comprising purified lantibiotic mutacin 1140 substantially free of any other *Streptococcus mutans* host proteins wherein the lantibiotic is isolated from a *S. mutans* strain and wherein the lantibiotic comprises:
   (a) antibiotic activity;
   (b) about 22 amino acid or modified amino acid residues;
   (c) at least 2 lanthionine residues;
   (d) at least 3 thioether bridges;
   (e) at least one 2,3-didehydroalanine amino acid residue;
   (f) at least one 2,3 didehydrobutyrine amino acid residue; and
   (g) an S-[aminovinyl]-cysteine.

2. A pharmaceutical preparation comprising purified lantibiotic mutacin 1140 substantially free of any other *Streptococcus mutans* host proteins wherein the lantibiotic is isolated from a *S. mutans* strain and wherein the lantibiotic comprises:
   (a) antibiotic activity;
   (b) about 22 amino acid or modified amino acid residues;
   (c) at least 2 lanthionine residues;
   (d) at least 3 thioether bridges;
   (e) at least one 2,3-didehydroalanine amino acid residue;
   (f) at least one 2,3 didehydrobutyrine amino acid residue; and
   (g) an S-[aminovinyl]-cysteine;
   and a pharmaceutically acceptable carrier.

3. A purified preparation of lantibiotic mutacin 1140 which is substantially free of the *Streptococcus mutans* host in which it was made and its other proteins, and wherein the lantibiotic is isolated from a *S. mutans* strain and wherein the lantibiotic comprises:
   (a) antibiotic activity;
   (b) about 22 amino acid or modified amino acid residues;
   (c) at least 2 lanthionine residues;
   (d) at least 3 thioether bridges;
   (e) at least one 2,3-didehydroalanine amino acid residue;
   (f) at least one 2,3 didehydrobutyrine amino acid residue; and
   (g) an S-[aminovinyl]-cysteine.

4. A dentifrice comprised of the preparation of claim 3 and a carrier.

5. A method for controlling microbial growth comprising applying an effective amount of the preparation of claim 3 to the area in which it is desired to control microbial growth.

6. A pharmaceutical preparation comprising purified lantibiotic mutacin 1140 pre-protein and a pharmaceutically acceptable carrier, wherein the purified pre-protein has the amino acid sequence set forth in SEQ ID NO:2.

7. A purified preparation of lantibiotic mutacin 1140 pre-protein, wherein the purified pre-protein has the amino acid sequence set forth in SEQ ID NO:2.

8. A method of controlling the growth of a microorganism in an animal comprising administering to the animal a composition comprising the composition of claim 1.

9. The method of claim 8, wherein the animal is a human.

10. A method of treating an animal having a bacterial infection comprising administering to the animal a composition comprising the composition of claim 1, whereby the infection is controlled.

11. The method of claim 10, wherein the animal is a human.

* * * * *